United States Patent
Jorgensen

(10) Patent No.: US 8,431,382 B2
(45) Date of Patent: Apr. 30, 2013

(54) **CHLORAMPHENICOL RESISTANCE SELECTION IN *BACILLUS LICHENIFORMIS***

(75) Inventor: Steen Troels Jorgensen, Alleroed (DK)

(73) Assignee: Novozymes A/S, Bagovaerd (DK)

( * ) Notice: Subject to any disclaimer, the term of this patent is extended or adjusted under 35 U.S.C. 154(b) by 46 days.

(21) Appl. No.: 12/302,047

(22) PCT Filed: May 29, 2007

(86) PCT No.: PCT/EP2007/055190
§ 371 (c)(1),
(2), (4) Date: Nov. 24, 2008

(87) PCT Pub. No.: WO2007/138049
PCT Pub. Date: Dec. 6, 2007

(65) Prior Publication Data
US 2009/0280569 A1    Nov. 12, 2009

Related U.S. Application Data

(60) Provisional application No. 60/810,506, filed on Jun. 2, 2006.

(30) Foreign Application Priority Data

May 31, 2006    (DK) ................................ 2006 00742

(51) Int. Cl.
*C12N 1/20* (2006.01)
*C12N 15/74* (2006.01)
*C12N 9/10* (2006.01)
*C12N 15/00* (2006.01)
*C12Q 1/68* (2006.01)
*C12P 21/06* (2006.01)
*C07H 21/04* (2006.01)

(52) U.S. Cl.
USPC ................... 435/252.31; 435/6.18; 435/69.1; 435/193; 435/471; 435/320.1; 536/23.2

(58) Field of Classification Search ........................ None
See application file for complete search history.

(56) References Cited

U.S. PATENT DOCUMENTS

2002/0068352 A1*  6/2002  Svendsen et al. ............. 435/202
2008/0293607 A1* 11/2008  Jones et al. ................... 510/226

FOREIGN PATENT DOCUMENTS

| WO | WO 96/023073  | 8/1996  |
| WO | WO 03/083125  | 10/2003 |
| WO | WO 2005/111203 | 11/2005 |

OTHER PUBLICATIONS

EMBL/UniProt Accession No. Q65GV9, (created Oct. 25, 2004).*
Shaw et al. Primary structure of a chloramphenicol acetyltransferase specified by R plasmids. Nature. Dec. 20-27, 1979;282(5741):870-2.*
Veith et al., "The Complete Genome Sequence of *Bacillus licheniformis* DSM13, An Organism With Great Industrial Potential", Journal of Molecular Microbiology and Biotechnology, vol. 7, No. 4, pp. 204-211 (2004).
International Search Report for PCT/EP2007/055190.

* cited by examiner

*Primary Examiner* — Anand Desai
*Assistant Examiner* — Iqbal H Chowdhury
(74) *Attorney, Agent, or Firm* — Michael W Krenicky

(57) ABSTRACT

The present invention relates to a modified *Bacillus licheniformis* host cell, wherein one or more naturally occurring chromosomal chloramphenicol acetyl transferase encoding gene(s), cat, has been inactivated. The inactivation of the chromosomal cat gene(s) allows the use of chloramphenicol as an efficient selective agent in methods for DNA introduction into the modified cell.

36 Claims, 1 Drawing Sheet

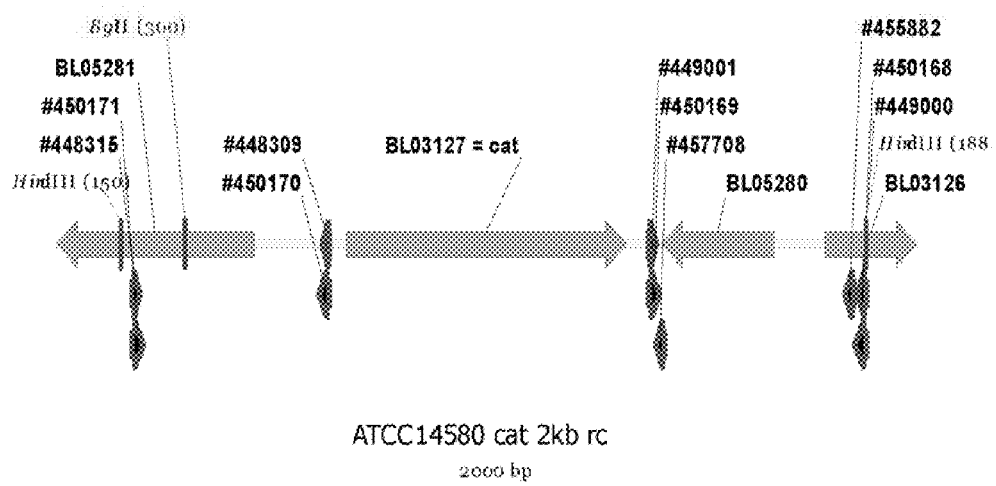
Schematic drawing of the *cat* gene region from ATCC14580.
ATCC14580 cat 2kb rc
2000 bp
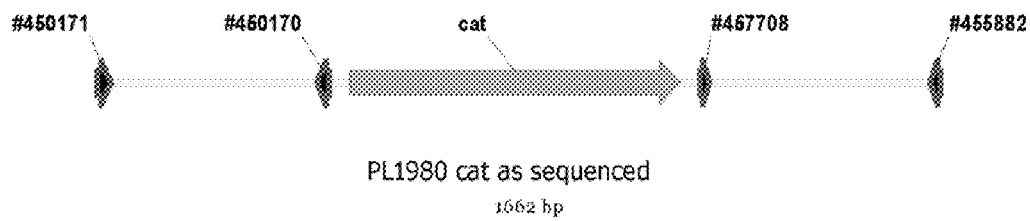
Figure 2. Schematic drawing of the *cat* gene region from PL1980.
PL1980 cat as sequenced
1662 bp

SEQUENCE LISTING

```
<160> NUMBER OF SEQ ID NOS: 24

<210> SEQ ID NO 1
<211> LENGTH: 2000
<212> TYPE: DNA
<213> ORGANISM: Bacillus licheniformis ATCC14580
<220> FEATURE:
<221> NAME/KEY: CDS
<222> LOCATION: (675)..(1322)
<223> OTHER INFORMATION: Encodes chloramphenicol acetyl transferase

<400> SEQUENCE: 1
atttctgcga tcgatcgttc tgaatgagca agcaaatcga ccgctttctc aatccttttc      60
tgcaggatgt attctgccgg cgagacgcct ttgattcgtt taaatgtccg ctgcaggtga     120
aaagggctga tatggcacct gtcagccaaa gcttgcagag acagcggatc gcgataagat     180
tcctcgatga tttccaccac acgctgtgcc agctcttcat ccggcagcag cgccccggcc     240
ggattgcagc gtttgcaggg gcggtaccct tctgataaag catcttttgc attgaaaaag     300
atctgcacat tgtcgatttg cggaactctc gatttgcagg aagggcggca aaatatgccg     360
gtcgttttga ccgcgtaata aaaaactccg tcataggcgg aatcgttttc cgtaatcgcc     420
cgccacattt caggcgtcaa tcgtgatttg ctgttcatat cttcacccg  atctatgtca     480 gtataaccta tatgacagcc ggaggtggag aggcggagaa cggcacagca agaagacaaa     540
```

```
gaagaagaga gactgttgcc tggacctccg aaacgcgcta caattcattt acaacacagg      600
atggggtgag aatattgccg gaatcagtga agcaggcctc ctaaaataaa aatctatatt      660
ttaggaggta aaac atg aat ttt caa aca atc gag ctt gac aca tgg tat       710
                Met Asn Phe Gln Thr Ile Glu Leu Asp Thr Trp Tyr
                  1               5                  10 aga aaa tct tat ttt gac cat tac atg aag gaa gcg aaa tgt tct ttc       758
Arg Lys Ser Tyr Phe Asp His Tyr Met Lys Glu Ala Lys Cys Ser Phe
         15                  20                  25 agc atc acg gca aac gtc aat gtg aca aat ttg ctc gcc gtg ctc aag       806
Ser Ile Thr Ala Asn Val Asn Val Thr Asn Leu Leu Ala Val Leu Lys
     30                  35                  40 aaa aag aag ctc aag ctg tat ccg gct ttt att tat atc gta tca agg       854
Lys Lys Lys Leu Lys Leu Tyr Pro Ala Phe Ile Tyr Ile Val Ser Arg
 45                  50                  55                  60 gtc att cat tcg cgc cct gag ttt aga aca acg ttt gat gac aaa gga       902
Val Ile His Ser Arg Pro Glu Phe Arg Thr Thr Phe Asp Asp Lys Gly
                 65                  70                  75 cag ctg ggt tat tgg gaa caa atg cat ccg tgc tat gcg att ttt cat       950
Gln Leu Gly Tyr Trp Glu Gln Met His Pro Cys Tyr Ala Ile Phe His
             80                  85                  90 cag gac gac caa acg ttt tcc gcc ctc tgg acg gaa tac tca gac gat       998
Gln Asp Asp Gln Thr Phe Ser Ala Leu Trp Thr Glu Tyr Ser Asp Asp
         95                  100                 105 ttt tcg cag ttt tat cat caa tat ctt ctg gac gcc gag cgc ttt gga      1046
Phe Ser Gln Phe Tyr His Gln Tyr Leu Leu Asp Ala Glu Arg Phe Gly
    110                 115                 120 gac aaa agg ggc ctt tgg gct aag ccg gac atc ccg ccc aat acg ttt      1094
Asp Lys Arg Gly Leu Trp Ala Lys Pro Asp Ile Pro Pro Asn Thr Phe
125                 130                 135                 140 tca gtt tct tct att cca tgg gtg cgc ttt tca aac ttc aat tta aac      1142
Ser Val Ser Ser Ile Pro Trp Val Arg Phe Ser Asn Phe Asn Leu Asn
                145                 150                 155 ctt gat aac agc gaa cac ttg ctg ccg att att aca aac ggg aaa tac      1190
Leu Asp Asn Ser Glu His Leu Leu Pro Ile Ile Thr Asn Gly Lys Tyr
            160                 165                 170 ttt tca gaa ggc agg gaa aca ttt ttg ccc gtt tcc ttg caa gtt cac      1238
Phe Ser Glu Gly Arg Glu Thr Phe Leu Pro Val Ser Leu Gln Val His
        175                 180                 185 cat gca gtg tgt gac ggc tat cat gcc ggc gct ttt ata aac gag ttg      1286
His Ala Val Cys Asp Gly Tyr His Ala Gly Ala Phe Ile Asn Glu Leu
    190                 195                 200 gaa cgg ctt gcc gcc gat tgt gag gag tgg ctt gtg tgacagagga           1332
Glu Arg Leu Ala Ala Asp Cys Glu Glu Trp Leu Val
205                 210                 215 aaggccgata tgattcggcc ttttttatat gtacttctta gcgggtctct taacatctct     1392
cactgctgtg tgattttact cacggcattt ggaacgccgg ctctcaacaa actttctgta     1452
gtgaaaatca tgaaccaaac ggatcgtcgg cctgattaac agctgaaagc tgccgatcac     1512
aaacatccat agtcccgccg gcttcagttc ctcggagaaa aagcagaagc tcccgacaag     1572
gaataaaagg ccgatgagaa aatcgtttaa tgtatgtaga actttgtatc ttttttttgaa    1632 aaagagttca tatcgtttgt tattgttttg cggcattgct tgatcactcc aatccttttta   1692 tttaccctgc cggaagccgg agtgaaacgc cggtatacat aggatttatg aattaggaaa    1752
acatatgggg aaataaacca tccaggagtg aaaaatatgc ggttattcat atgtgcatcg    1812
tgcctgttcg gcttgattgt tccgtcattt gaaacgaaag cgctgacgtt tgaagaattg    1872
ccggttaaac aagcttcaaa acaatgggaa gttcaaatcg gtaaagccga agccggaaac    1932
```

```
ggaatggcga aaccggaaaa aggagcgttt catacttatg ctgtcgaaat caaaaacatt    1992
ggacacga                                                             2000
```

<210> SEQ ID NO 2
<211> LENGTH: 216
<212> TYPE: PRT
<213> ORGANISM: Bacillus licheniformis ATCC14580

<400> SEQUENCE: 2

```
Met Asn Phe Gln Thr Ile Glu Leu Asp Thr Trp Tyr Arg Lys Ser Tyr
1               5                   10                  15

Phe Asp His Tyr Met Lys Glu Ala Lys Cys Ser Phe Ser Ile Thr Ala
            20                  25                  30

Asn Val Asn Val Thr Asn Leu Leu Ala Val Leu Lys Lys Lys Lys Leu
        35                  40                  45

Lys Leu Tyr Pro Ala Phe Ile Tyr Ile Val Ser Arg Val Ile His Ser
    50                  55                  60

Arg Pro Glu Phe Arg Thr Thr Phe Asp Asp Lys Gly Gln Leu Gly Tyr
65                  70                  75                  80

Trp Glu Gln Met His Pro Cys Tyr Ala Ile Phe His Gln Asp Asp Gln
                85                  90                  95

Thr Phe Ser Ala Leu Trp Thr Glu Tyr Ser Asp Asp Phe Ser Gln Phe
            100                 105                 110

Tyr His Gln Tyr Leu Leu Asp Ala Glu Arg Phe Gly Asp Lys Arg Gly
        115                 120                 125

Leu Trp Ala Lys Pro Asp Ile Pro Pro Asn Thr Phe Ser Val Ser Ser
    130                 135                 140

Ile Pro Trp Val Arg Phe Ser Asn Phe Asn Leu Asn Leu Asp Asn Ser
145                 150                 155                 160

Glu His Leu Leu Pro Ile Ile Thr Asn Gly Lys Tyr Phe Ser Glu Gly
                165                 170                 175

Arg Glu Thr Phe Leu Pro Val Ser Leu Gln Val His His Ala Val Cys
            180                 185                 190

Asp Gly Tyr His Ala Gly Ala Phe Ile Asn Glu Leu Glu Arg Leu Ala
        195                 200                 205

Ala Asp Cys Glu Glu Trp Leu Val
    210                 215
```

<210> SEQ ID NO 3
<211> LENGTH: 29
<212> TYPE: DNA
<213> ORGANISM: artificial sequence
<220> FEATURE:
<223> OTHER INFORMATION: Primer #449000

<400> SEQUENCE: 3

```
cagtgaattc gtttaaccgg caattcttc                                        29
```

<210> SEQ ID NO 4
<211> LENGTH: 29
<212> TYPE: DNA
<213> ORGANISM: artificial sequence
<220> FEATURE:
<223> OTHER INFORMATION: Primer #449001

<400> SEQUENCE: 4

```
cagtgtcgac gtctcttaac atctctcac                                        29
```

<210> SEQ ID NO 5

```
<211> LENGTH: 27
<212> TYPE: DNA
<213> ORGANISM: artificial sequence
<220> FEATURE:
<223> OTHER INFORMATION: Primer #448309

<400> SEQUENCE: 5
cagtgtcgac ctgcttcact gattccg                                      27

<210> SEQ ID NO 6
<211> LENGTH: 29
<212> TYPE: DNA
<213> ORGANISM: artificial sequence
<220> FEATURE:
<223> OTHER INFORMATION: Primer #448315

<400> SEQUENCE: 6
cagtaagctt aagattcctc gatgatttc                                    29

<210> SEQ ID NO 7
<211> LENGTH: 36
<212> TYPE: DNA
<213> ORGANISM: artificial sequence
<220> FEATURE:
<223> OTHER INFORMATION: Primer #450168

<400> SEQUENCE: 7
cagtgaattc gtttaaccgg caattcttca aacgtc                            36

<210> SEQ ID NO 8
<211> LENGTH: 36
<212> TYPE: DNA
<213> ORGANISM: artificial sequence
<220> FEATURE:
<223> OTHER INFORMATION: Primer #450169

<400> SEQUENCE: 8
cagtgtcgac gtctcttaac atctctcact gctgtg                            36

<210> SEQ ID NO 9
<211> LENGTH: 35
<212> TYPE: DNA
<213> ORGANISM: artificial sequence
<220> FEATURE:
<223> OTHER INFORMATION: Primer #450170

<400> SEQUENCE: 9
cagtgtcgac cgcttcactg attccggcaa tattc                             35

<210> SEQ ID NO 10
<211> LENGTH: 37
<212> TYPE: DNA
<213> ORGANISM: artificial sequence
<220> FEATURE:
<223> OTHER INFORMATION: Primer #450171

<400> SEQUENCE: 10
cagtaagctt aagattcctc gatgatttcc accacac                           37

<210> SEQ ID NO 11
<211> LENGTH: 31
<212> TYPE: DNA
<213> ORGANISM: artificial sequence
<220> FEATURE:
<223> OTHER INFORMATION: Primer #455882

<400> SEQUENCE: 11
```

-continued

```
cagtgaattc cgctttcgtt tcaaatgacg g                                    31
```

```
<210> SEQ ID NO 12
<211> LENGTH: 1662
<212> TYPE: DNA
<213> ORGANISM: Bacillus licheniformis PL1980
<220> FEATURE:
<221> NAME/KEY: CDS
<222> LOCATION: (499)..(1146)
<223> OTHER INFORMATION: Encodes chloramphenicol acetyl transferase

<400> SEQUENCE: 12
```

```
taagattcct cgatgatttc caccacacgc tgtgccagct cttcatccgg cagcagcgct      60
ccggcgggat tgcagcgttt gcagggycgg aaccttctg ataaagcatc ttttgcattg      120
aaaaaaatct gcacattgtc gatttgcgga actctcgatt tgcaggatgg gcggcaaaat    180
atgccggtcg ttttgaccgc gtaataaaaa actccgtcat aggcggaatc gttttccgta    240
attgcccgcc acatttcagg cgtcaatcgt gatttgctgt tcatatcttc accccgatat    300
atgtcagtat aacctaaatg acagccgggg gtgagagacg gagaacggca cagcaagaat    360
acaaagaagg agggatcggt tgcttcggcc tccgaaacgc gctacaattc atttacaata    420
caggatgagg tgagaatatt gccgaaatca gtgaagcagt cctcctaaaa taaaaatcta    480
tattttagga ggtaaaac atg aat ttt caa aca atc gag ctt gac act tgg      531
                    Met Asn Phe Gln Thr Ile Glu Leu Asp Thr Trp
                     1               5                  10 tat aga aaa tcc tat ttt gac cat tac atg aag gat gcg aaa tgt tct      579
Tyr Arg Lys Ser Tyr Phe Asp His Tyr Met Lys Asp Ala Lys Cys Ser
            15                  20                  25 ttc tgc atc acg gca aac gtc aat gtg aca aat ttg ctc gcc ttg ctc      627
Phe Cys Ile Thr Ala Asn Val Asn Val Thr Asn Leu Leu Ala Leu Leu
        30                  35                  40 aag aaa aag aag atc aag ctg tac ccg gct ttt att tat atc gta tca      675
Lys Lys Lys Lys Ile Lys Leu Tyr Pro Ala Phe Ile Tyr Ile Val Ser
    45                  50                  55 agg gtc att cat tcg cgc cct gag ttt aga aca act ttt gat gac aaa      723
Arg Val Ile His Ser Arg Pro Glu Phe Arg Thr Thr Phe Asp Asp Lys
60                  65                  70                  75 gga cgg ctg ggt tat tgg gaa caa atg cat ccg tgc tat gcg att ttt      771
Gly Arg Leu Gly Tyr Trp Glu Gln Met His Pro Cys Tyr Ala Ile Phe
                80                  85                  90 cat cag gac gac caa acg ttt tcc gcc ctc tgg acg gaa tac tca gac      819
His Gln Asp Asp Gln Thr Phe Ser Ala Leu Trp Thr Glu Tyr Ser Asp
            95                  100                 105 gat ttt tcg cag ttt tat cat caa tat ctt ctg gac gct gag cgc ttt      867
Asp Phe Ser Gln Phe Tyr His Gln Tyr Leu Leu Asp Ala Glu Arg Phe
        110                 115                 120 gga gac aaa agg ggc ctt tgg gct aag ccg gac atc ccg ccc aat acg      915
Gly Asp Lys Arg Gly Leu Trp Ala Lys Pro Asp Ile Pro Pro Asn Thr
    125                 130                 135 ttc tca gtt tca tct att cca tgg gtg agc ttt aca aac ttc aat tta      963
Phe Ser Val Ser Ser Ile Pro Trp Val Ser Phe Thr Asn Phe Asn Leu
140                 145                 150                 155 aac ctt gat aac agc gaa cac ttg ctg ccg att atc aca aac ggg aaa     1011
Asn Leu Asp Asn Ser Glu His Leu Leu Pro Ile Ile Thr Asn Gly Lys
                160                 165                 170 tac ttt tca gaa ggc cgg gaa aca ttt ttg ccc gtt tcc ctg caa gta     1059
Tyr Phe Ser Glu Gly Arg Glu Thr Phe Leu Pro Val Ser Leu Gln Val
            175                 180                 185 cac cat gcc gtg tgt gac ggc tat cat gcc ggc gcc ttc atg aac gag    1107
His His Ala Val Cys Asp Gly Tyr His Ala Gly Ala Phe Met Asn Glu
```

```
                190                 195                 200
ttg gca cgg ctt gcc gcc gat tgt aag gag tgg ctt gtg tgacagagga    1156
Leu Ala Arg Leu Ala Ala Asp Cys Lys Glu Trp Leu Val
    205                 210                 215 aaggccgata tgattcggcc ttttttatat gcgctgctta gcggtcttac tgtggtgtgt    1216
ttactcccgg catttggaac gccggctctc aacaaacttt ctgtagtgaa atcatgaac     1276
caaacggatc gtcggcctga ttaacagctg aaagctgccg atcacaaaca tccatagtcc    1336
cgccggcttc agttcctcgg agaaaaagca gaagctcccg acaaggaata aaaggccgat    1396
gagaaaatcg tttaatatat gtagaacttt gtatcttttt ttgaaaaaga gttcatatcg    1456
attgttattg ttttgcggca ttgcttgatc actccaatcc ttttatttac cctgccggaa    1516
gccggagtga aaagccggta tacataggat ttatgaatta ggaaaacata tgggaaata     1576
aaccatccag gagtgaaaaa tatgcggtta ttcatatgtg catcgtgcct gttcggcttg    1636
attgttccgt catttgaaac gaaagc                                         1662
```

<210> SEQ ID NO 13
<211> LENGTH: 216
<212> TYPE: PRT
<213> ORGANISM: Bacillus licheniformis PL1980

<400> SEQUENCE: 13

```
Met Asn Phe Gln Thr Ile Glu Leu Asp Thr Trp Tyr Arg Lys Ser Tyr
1               5                   10                  15

Phe Asp His Tyr Met Lys Asp Ala Lys Cys Ser Phe Cys Ile Thr Ala
            20                  25                  30

Asn Val Asn Val Thr Asn Leu Leu Ala Leu Leu Lys Lys Lys Lys Ile
        35                  40                  45

Lys Leu Tyr Pro Ala Phe Ile Tyr Ile Val Ser Arg Val Ile His Ser
    50                  55                  60

Arg Pro Glu Phe Arg Thr Thr Phe Asp Asp Lys Gly Arg Leu Gly Tyr
65                  70                  75                  80

Trp Glu Gln Met His Pro Cys Tyr Ala Ile Phe His Gln Asp Asp Gln
                85                  90                  95

Thr Phe Ser Ala Leu Trp Thr Glu Tyr Ser Asp Asp Phe Ser Gln Phe
            100                 105                 110

Tyr His Gln Tyr Leu Leu Asp Ala Glu Arg Phe Gly Asp Lys Arg Gly
        115                 120                 125

Leu Trp Ala Lys Pro Asp Ile Pro Pro Asn Thr Phe Ser Val Ser Ser
    130                 135                 140

Ile Pro Trp Val Ser Phe Thr Asn Phe Asn Leu Asn Leu Asp Asn Ser
145                 150                 155                 160

Glu His Leu Leu Pro Ile Ile Thr Asn Gly Lys Tyr Phe Ser Glu Gly
                165                 170                 175

Arg Glu Thr Phe Leu Pro Val Ser Leu Gln Val His His Ala Val Cys
            180                 185                 190

Asp Gly Tyr His Ala Gly Ala Phe Met Asn Glu Leu Ala Arg Leu Ala
        195                 200                 205

Ala Asp Cys Lys Glu Trp Leu Val
    210                 215
```

<210> SEQ ID NO 14
<211> LENGTH: 29
<212> TYPE: DNA
<213> ORGANISM: artificial sequence
<220> FEATURE:

<223> OTHER INFORMATION: Primer #457708

<400> SEQUENCE: 14
cagtgtcgac ctgcttagcg gtcttactg                                    29

<210> SEQ ID NO 15
<211> LENGTH: 41
<212> TYPE: DNA
<213> ORGANISM: artificial sequence
<220> FEATURE:
<223> OTHER INFORMATION: Primer #448697

<400> SEQUENCE: 15
gactaagctt agatcttcac ttccttattt tgttgtaagt a                      41

<210> SEQ ID NO 16
<211> LENGTH: 31
<212> TYPE: DNA
<213> ORGANISM: artificial sequence
<220> FEATURE:
<223> OTHER INFORMATION: Primer #448698

<400> SEQUENCE: 16
gactgaattc gtcgatcact ttctgccact c                                 31

<210> SEQ ID NO 17
<211> LENGTH: 54
<212> TYPE: DNA
<213> ORGANISM: artificial sequence
<220> FEATURE:
<223> OTHER INFORMATION: Primer #448699

<400> SEQUENCE: 17
gactgaattc agatctgcta gcacgcgtgc ggccgcacga agacagcccg cttc        54

<210> SEQ ID NO 18
<211> LENGTH: 32
<212> TYPE: DNA
<213> ORGANISM: artificial sequence
<220> FEATURE:
<223> OTHER INFORMATION: Primer #448700

<400> SEQUENCE: 18
gactaagctt cataaattct cggatacaac ac                                32

<210> SEQ ID NO 19
<211> LENGTH: 37
<212> TYPE: DNA
<213> ORGANISM: artificial sequence
<220> FEATURE:
<223> OTHER INFORMATION: Primer #448716

<400> SEQUENCE: 19
gactggatcc atgaacttta ataaaattga tttagac                           37

<210> SEQ ID NO 20
<211> LENGTH: 44
<212> TYPE: DNA
<213> ORGANISM: artificial sequence
<220> FEATURE:
<223> OTHER INFORMATION: Primer #448718

<400> SEQUENCE: 20
gactgaattc gctagcacgc gttataaaag ccagtcatta ggcc                   44

<210> SEQ ID NO 21

-continued

```
<211> LENGTH: 1612
<212> TYPE: DNA
<213> ORGANISM: Bacillus licheniformis 9945A
<220> FEATURE:
<221> NAME/KEY: CDS
<222> LOCATION: (457)..(1104)
<223> OTHER INFORMATION: Encodes chloramphenicol acetyl transferase

<400> SEQUENCE: 21
tccggcagca gcatcccggc cggattgcag cgtttgcagg ggcggtaccc ttctgataaa      60
gcatcttttg cattgaaaaa gatttgcaca ttttcgattt gcggaactct cgatttgcag     120
gaagggcggc aaaatatccc ggtcgttttg accgcgtaat aaaaaactcc gtcataggcg     180
gaatcgtttt ccgtaatcgc ccgccacctt tcaggcgtca atcgtgattt gctgttcata     240
tcttcacccc gatctatgtc agtataacct aaatgacagc cggaggtgga gaggcgggga     300
atggcacagc aagaagacaa agaagaagag ggacggttgc ctgcgtctcc gaaacgcgct     360
acaattcatt tgcaatacag gatgaggtga gaatattgcc gaaatcagag aagcaggcct     420
cctaaaataa aaaagctata ttttaggagg taaaac atg aat ttt caa aca atc      474
                                         Met Asn Phe Gln Thr Ile
                                          1               5 gat ctc gac act tgg tat aga aaa tct tat ttt gac cat tac atg aag      522
Asp Leu Asp Thr Trp Tyr Arg Lys Ser Tyr Phe Asp His Tyr Met Lys
        10                  15                  20 gaa gcg aaa tgt tct ttc agt ata acg aca aac gtc aat gtg acc aat      570
Glu Ala Lys Cys Ser Phe Ser Ile Thr Thr Asn Val Asn Val Thr Asn
25                  30                  35 ttg ctt gcc gtg ctc aag aaa aag aag atc aag ctg tac ccg gtt ttt      618
Leu Leu Ala Val Leu Lys Lys Lys Lys Ile Lys Leu Tyr Pro Val Phe
            40                  45                  50 att tat atc gta tca agg gcc att cat tcg cgt cct gag ttt aga aca      666
Ile Tyr Ile Val Ser Arg Ala Ile His Ser Arg Pro Glu Phe Arg Thr
55                  60                  65                  70 act ttt aac gac aaa gga cag ctg gga tat tgg gaa caa atg cac ccg      714
Thr Phe Asn Asp Lys Gly Gln Leu Gly Tyr Trp Glu Gln Met His Pro
                75                  80                  85 tgc tat acg att ttt cat cag gac gac caa acg ttt tcc gcc ctc tgg      762
Cys Tyr Thr Ile Phe His Gln Asp Asp Gln Thr Phe Ser Ala Leu Trp
            90                  95                 100 aca gaa tac tca aat gat ttc tcg cgg ttt tat cgt caa tat ctt cag      810
Thr Glu Tyr Ser Asn Asp Phe Ser Arg Phe Tyr Arg Gln Tyr Leu Gln
        105                 110                 115 gat gcc gag cgc ttt gga gac aaa aag ggc tta tgg gct aag ccg gac      858
Asp Ala Glu Arg Phe Gly Asp Lys Lys Gly Leu Trp Ala Lys Pro Asp
    120                 125                 130 atc ccg ccc aat gcg ttt tca gtt tct tct att cca tgg gtg cgc ttt      906
Ile Pro Pro Asn Ala Phe Ser Val Ser Ser Ile Pro Trp Val Arg Phe
135                 140                 145                 150 aca aac ttt aat tta aac cta gat aac agc gaa cac ttg ctg ccg att      954
Thr Asn Phe Asn Leu Asn Leu Asp Asn Ser Glu His Leu Leu Pro Ile
                155                 160                 165 att aca aac ggg aaa tac ttt tca gaa ggc ggt gaa aca ttt ttg ccg     1002
Ile Thr Asn Gly Lys Tyr Phe Ser Glu Gly Gly Glu Thr Phe Leu Pro
            170                 175                 180 gtt tcc ctg caa gta cac cat gca gtg tgt gac ggc tat cat gcc ggc     1050
Val Ser Leu Gln Val His His Ala Val Cys Asp Gly Tyr His Ala Gly
        185                 190                 195 gct ttt atg aac gag ttg gaa cgg ctt gcc gcc gat tgt gag gag tgg     1098
Ala Phe Met Asn Glu Leu Glu Arg Leu Ala Ala Asp Cys Glu Glu Trp
    200                 205                 210
```

```
ctt atg tgacagagga aaggccgatt ggattcggcc ttttttatat gcacttctta    1154
Leu Met
215 gcgggtctcc taccatctct ccctgctgtt taaatttact cacgggattt ggaacgccgg   1214 ctctcaacaa acttccggta atgaaaatca tgaaccaaac ggatcgtcgg cctgattaac   1274 agctgaaagc tgccgatcac aaacatccat attcccgccg gcttcagttc ctcgaagaaa   1334 aaacagaagc tcccgacaag gaataaaaga ccgataagaa atcgtttaa tgtatgaaga    1394 actttgtatc tttttttgaa aaagagttcg tatcgatcat tgtggttttg cggcattgct   1454 tgatccctcc agtccttta ttaccctgcc ggaagcagga gtgaaacgtc ggtatgcata    1514 ggatttatga ataaggaaaa acatatagg acatcgacca tcgaggagtg aaaaatatgc    1574 ggctattcat atgtgcattg tgcctgttca gcatgatt                            1612
```

```
<210> SEQ ID NO 22
<211> LENGTH: 216
<212> TYPE: PRT
<213> ORGANISM: Bacillus licheniformis 9945A

<400> SEQUENCE: 22
```

Met Asn Phe Gln Thr Ile Asp Leu Asp Thr Trp Tyr Arg Lys Ser Tyr
1               5                  10                  15

Phe Asp His Tyr Met Lys Glu Ala Lys Cys Ser Phe Ser Ile Thr Thr
            20                  25                  30

Asn Val Asn Val Thr Asn Leu Leu Ala Val Leu Lys Lys Lys Lys Ile
        35                  40                  45

Lys Leu Tyr Pro Val Phe Ile Tyr Ile Val Ser Arg Ala Ile His Ser
50                  55                  60

Arg Pro Glu Phe Arg Thr Thr Phe Asn Asp Lys Gly Gln Leu Gly Tyr
65                  70                  75                  80

Trp Glu Gln Met His Pro Cys Tyr Thr Ile Phe His Gln Asp Asp Gln
                85                  90                  95

Thr Phe Ser Ala Leu Trp Thr Glu Tyr Ser Asn Asp Phe Ser Arg Phe
            100                 105                 110

Tyr Arg Gln Tyr Leu Gln Asp Ala Glu Arg Phe Gly Asp Lys Lys Gly
        115                 120                 125

Leu Trp Ala Lys Pro Asp Ile Pro Pro Asn Ala Phe Ser Val Ser Ser
130                 135                 140

Ile Pro Trp Val Arg Phe Thr Asn Phe Asn Leu Asn Leu Asp Asn Ser
145                 150                 155                 160

Glu His Leu Leu Pro Ile Ile Thr Asn Gly Lys Tyr Phe Ser Glu Gly
                165                 170                 175

Gly Glu Thr Phe Leu Pro Val Ser Leu Gln Val His His Ala Val Cys
            180                 185                 190

Asp Gly Tyr His Ala Gly Ala Phe Met Asn Glu Leu Glu Arg Leu Ala
        195                 200                 205

Ala Asp Cys Glu Glu Trp Leu Met
    210                 215

```
<210> SEQ ID NO 23
<211> LENGTH: 602
<212> TYPE: DNA
<213> ORGANISM: Bacillus licheniformis
<220> FEATURE:
<221> NAME/KEY: misc_feature
<222> LOCATION: (1)..(599)
<223> OTHER INFORMATION: Encodes the chloramphenicol acetyl transferase
      shown in SEQ ID NO: 24.
```

<400> SEQUENCE: 23

```
atgaattttc aaacaatcga gcttgacaca tggtatagaa aatcttattt tgaccattac    60
atgaaggaag cgaaatgttc tttcagcatc acggcaaacg tcaatgtgac aaatttgctc   120
gccgtgctca agaaaaagaa gctcaagctg tatccggctt ttatttatat cgtatcaagg   180
gtcattcatt cgcgccctga gtttagaaca acgtttgatg acaaaggaag ctgggttatt   240
gggaacaaat gcatccgtgc tatgcgattt ttcatcagga cgaccaaacg ttttccgccc   300
tctggacgga atactcagac gattttcgc agttttatca tcaatatctt ctggacgccg   360
agcgctttgg agacaaaagg ggcctttggg ctaagccgga catcccgccc aatacgtttt   420
cagtttcttc tattccatgg gtgcgctttt caacattcaa tttaaacctt gataacagcg   480
aacacttgct gccgattatt acaaacggga atactttc agaaggcagg gaaacatttt   540
tgcccgtttc ctgcaagttc accatgcagt gtgtgacggc tatcatgccg gcgcttttat   600
aa                                                                 602
```

<210> SEQ ID NO 24
<211> LENGTH: 200
<212> TYPE: PRT
<213> ORGANISM: Bacillus licheniformis

<400> SEQUENCE: 24

```
Met Asn Phe Gln Thr Ile Glu Leu Asp Thr Trp Tyr Arg Lys Ser Tyr
1               5                   10                  15

Phe Asp His Tyr Met Lys Glu Ala Lys Cys Ser Phe Ser Ile Thr Ala
            20                  25                  30

Asn Val Asn Val Thr Asn Leu Leu Ala Val Leu Lys Lys Lys Lys Leu
        35                  40                  45

Lys Leu Tyr Pro Ala Phe Ile Tyr Ile Val Ser Arg Val Ile His Ser
    50                  55                  60

Arg Pro Glu Phe Arg Thr Thr Phe Asp Asp Lys Gly Gln Leu Gly Tyr
65                  70                  75                  80

Trp Glu Gln Met His Pro Cys Tyr Ala Ile Phe His Gln Asp Asp Gln
                85                  90                  95

Thr Phe Ser Ala Leu Trp Thr Glu Tyr Ser Asp Phe Ser Gln Phe
            100                 105                 110

Tyr His Gln Tyr Leu Leu Asp Ala Glu Arg Phe Gly Asp Lys Arg Gly
        115                 120                 125

Leu Trp Ala Lys Pro Asp Ile Pro Pro Asn Thr Phe Ser Val Ser Ser
    130                 135                 140

Ile Pro Trp Val Arg Phe Ser Thr Phe Asn Leu Asn Leu Asp Asn Ser
145                 150                 155                 160

Glu His Leu Leu Pro Ile Ile Thr Asn Gly Lys Tyr Phe Ser Glu Gly
                165                 170                 175

Arg Glu Thr Phe Leu Pro Val Ser Cys Lys Phe Thr Met Gln Cys Val
            180                 185                 190

Thr Ala Ile Met Pro Ala Leu Leu
        195                 200
```

CHLORAMPHENICOL RESISTANCE SELECTION IN BACILLUS LICHENIFORMIS

CROSS-REFERENCE TO RELATED APPLICATIONS

This application is a 35 U.S.C. 371 national application of PCT/EP2007/055190 filed May 29, 2007, which claims priority or the benefit under 35 U.S.C. 119 of Danish application no. PA 2006 00742 filed May 31, 2006 and U.S. provisional application No. 60/810,506 filed Jun. 2, 2006 the contents of which are fully incorporated herein by reference.

SEQUENCE LISTING

This invention comprises a sequence listing.

FIELD OF THE INVENTION

The present invention relates to a modified *Bacillus licheniformis* host cell, wherein naturally occurring chromosomal chloramphenicol acetyl transferase gene(s), cat, has been inactivated. The inactivation of the chromosomal cat gene(s) allows the use of chloramphenicol as an efficient selective agent in methods for DNA introduction into the modified cell.

BACKGROUND OF THE INVENTION

In the industrial production of polypeptides it is of interest to achieve a product yield as high as possible. One way to increase the yield is to increase the copy number of a gene encoding a polypeptide of interest. This can be done by placing the gene on a high copy number plasmid, however plasmids are unstable and are often lost from the host cells if there is no selective pressure during the cultivation of the host cells. Another way to increase the copy number of the gene of interest is to integrate it into the host cell chromosome in multiple copies.

The cat-gene (chloramphenicol acetyl transferase) from plasmid pC194 is routinely used as a selective marker in *Bacillus* transformation. *Bacillus licheniformis*, however, exhibits chloramphenicol resistance to an extent which hampers the use of chloramphenicol resistance genes for selection of transformants, whether by protoplast transformation, conjugation or electroporation.

Genome sequencing has revealed that several different *B. licheniformis* strains harbour a sequence in the chromosome which has some homology with known chloramphenicol resistance genes. The homologous sequence is located at position at position 2720850 to 2721500 in the EMBL *Bacillus licheniformis* ATCC14580 sequence entry, accession number cp000002.

SUMMARY OF THE INVENTION

A putative cat-gene, along with flanking DNA, was identified in the EMBL *Bacillus licheniformis* ATCC14580 sequence entry, accession number cp000002. A schematic drawing is shown in FIG. 1.

We wanted to explore, whether the deletion of this putative cat-gene from the chromosome of *B. licheniformis* strains would allow the use of chloramphenicol for selection of DNA introduction into such cat-deleted strains.

Homologues to the cat-gene were identified in a number of different *B. licheniformis* strains from various sources, and these were inactivated in the chromosomes of those strains to provide modified cat-sensitive strains.

The present invention relates to methods of introducing genetic material comprising a chloramphenicol resistance marker into a modified *Bacillus licheniformis* host cells, wherein a naturally occurring chromosomal chloramphenicol resistance gene, cat, has been inactivated. The presence of this gene in its active form otherwise hampers the use of chloramphenicol for selection purposes. Having a natural antibiotic resistance encoding gene in an industrial production host cell may also be a cause for concern in certain applications, e.g., for regulatory purposes.

Accordingly, in a first aspect the invention relates to a method for introducing a recombinant DNA construct into a modified *Bacillus licheniformis* host cell, the method comprising:

a) providing a modified *Bacillus licheniformis* host cell, wherein one or more endogenous genomic chloramphenicol acetyl transferase encoding gene(s) has been inactivated;

b) introducing a recombinant DNA construct comprising a selection marker encoding a chloramphenicol acetyl transferase into the modified host cell;

c) cultivating the host cell of step (b) in a growth-medium comprising an inhibitory concentration of chloramphenicol; and d) selecting a host cell comprising the DNA construct that is capable of growing in the medium of step (c).

In a second aspect, the invention relates to a modified *Bacillus licheniformis* host cell, wherein one or more genomic chloramphenicol acetyl transferase gene(s) has been inactivated, comprising a recombinant DNA construct carrying a selection marker encoding a chloramphenicol acetyl transferase.

BRIEF DESCRIPTION OF DRAWINGS

FIG. 1 shows a schematic drawing of the cat gene region from *B. licheniformis* ATCC14580 with indication of the primers used herein.

FIG. 2 shows a schematic drawing of the cat gene region from *B. licheniformis* PL1980 with indication of the primers used herein.

DEFINITIONS

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases, the sequence of the polynucleotide is the actual sequence of the bases read from the 5' to the 3' end of the polymer. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A DNA "coding sequence" or an "open reading frame (ORF)" is a double-stranded DNA sequence which is transcribed and translated into a polypeptide in a cell in vitro or in vivo when placed under the control of appropriate regulatory sequences. The ORF "encodes" the polypeptide. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell e.g. in eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered "non-functional" if the polypeptide that the gene encodes can no longer be expressed in a functional form. Such non-functionality of a gene can be induced by a wide variety of genetic manipulations or alterations as known in the art, some of which are described in Sambrook et al. vide supra. Partial deletions within the ORF of a gene will often render the gene non-functional, as will mutations e.g. substitutions, insertions, frameshifts etc.

"Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

"Heterologous" DNA in a host cell, in the present context refers to exogenous DNA not originating from the cell.

As used herein the term "nucleic acid construct" or "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., Science 239 (1988), 487-491.

The term nucleic acid construct may be synonymous with the term "expression cassette" when the nucleic acid construct contains the control sequences necessary for expression of a coding sequence of the present invention The term "control sequences" is defined herein to include all components that are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence that is recognized by a host cell for expression of the nucleic acid sequence. The promoter sequence contains transcription and translation control sequences that mediate the expression of the polypeptide. The promoter may be any nucleic acid sequence that shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide-coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide-coding region naturally linked in translation reading frame with the segment of the coding region which encodes the secreted polypeptide. Alternatively, the 5' end of the coding sequence may contain a signal peptide-coding region which is foreign to that portion of the coding sequence which encodes the secreted polypeptide. A foreign signal peptide-coding region may be required where the coding sequence does not normally contain a signal peptide-coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide-coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN AMYLASE GENE, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731), as well as the tac promoter (DeBoer et al., 1983, Proceedings of the National Academy of Sciences USA 80:21-25). Further promoters are described in "Useful proteins from recombinant bacteria" in Scientific American, 1980, 242:74-94; and in Sambrook et al., 1989, supra.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more "selectable markers" which permit easy selection of transformed cells. A selectable marker is a gene the product of which provides for biocide, antibiotic or viral resistance, resistance to heavy metals, prototrophy to auxotrophs, and the like.

A "conditionally essential gene" may function as a "non-antibiotic selectable marker". Non-limiting examples of bacterial conditionally essential selectable markers are the dal genes from *Bacillus subtilis* or *Bacillus licheniformis*, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other non-limiting examples of conditionally essential genes are given below.

Antibiotic selectable markers confer antibiotic resistance to such antibiotics as ampicillin, kanamycin, chloramphenicol, erythromycin, tetracycline, neomycin, hygromycin or methotrexate.

Furthermore, selection may be accomplished by co-transformation, e.g., as described in WO 91/17243, where the selectable marker is on a separate vector.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. The origin of replication may be one having a mutation which makes its functioning temperature-sensitive in the host cell (see, e.g., Ehrlich, 1978, Proceedings of the National Academy of Sciences USA 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The transformation of a bacterial host cell may, for instance, be effected by protoplast transformation (see, e.g., Chang and Cohen, 1979, Molecular General Genetics 168: 111-115), by using competent cells (see, e.g., Young and Spizizin, 1961, Journal of Bacteriology 81:823-829, or Dubnar and Davidoff-Abelson, 1971, Journal of Molecular Biology 56:209-221), by electroporation (see, e.g., Shigekawa and Dower, 1988, Biotechniques 6:742-751), or by conjugation (see, e.g., Koehler and Thorne, 1987, Journal of Bacteriology 169:5771-5278).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

DETAILED DESCRIPTION OF THE INVENTION

As mentioned above, the invention relates in a first aspect to a method for introducing a recombinant DNA construct into a modified Bacillus licheniformis host cell, the method comprising:
a) providing a modified Bacillus licheniformis host cell, wherein one or more endogenous genomic chloramphenicol acetyl transferase encoding gene(s) has been inactivated;
b) introducing a recombinant DNA construct comprising a selection marker encoding a chloramphenicol acetyl transferase into the modified host cell;
c) cultivating the host cell of step (b) in a growth-medium comprising an inhibitory concentration of chloramphenicol; and
d) selecting a host cell comprising the DNA construct that is capable of growing in the medium of step (c).

Another aspect of the invention relates to a modified Bacillus licheniformis host cell, wherein one or more genomic chloramphenicol acetyl transferase gene(s) has been inactivated, comprising a recombinant DNA construct carrying a selection marker encoding a chloramphenicol acetyl transferase.

It is to be understood that the preferred embodiments listed below are by no means exhaustive, they can be combined in various ways, as the skilled person would immediately appreciate. The skilled person would be well aware of the possibility of combining these preferred embodiments with other technical features well-known in the art of introducing genetic material into Bacillus cells, but not listed explicitly herein, such as described in various patent disclosures, e.g., WO 2002/000907, WO 2001/090393, WO 1993/010249, WO 1999/043835, WO 1994/019471, WO 2003/055996, WO 1991/009129, WO 1994/014968, and/or WO 1996/023073, all of which are incorporated herein by reference.

In preferred embodiments of the invention the recombinant DNA construct is a plasmid or a linearized plasmid, preferably a linearized and concatamerized plasmid.

In another preferred embodiment of the invention the recombinant DNA construct further comprises a polynucleotide encoding a polypeptide of interest, preferably an enzyme, more preferably an amylolytic enzyme, a lipolytic enzyme, a proteolytic enzyme, a cellulytic enzyme, an oxidoreductase or a plant cell-wall degrading enzyme, and even more preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

Still another preferred embodiment relates to the first and second aspects, wherein the one or more genomic chloramphenicol acetyl transferase gene(s) encodes a chloramphenicol acetyl transferase comprising an amino acid sequence which is at least 80% identical, 85% identical, 90% identical, 92% identical, 94% identical, 96% identical, 98% identical, or at least 99% identical to the sequence shown in SEQ ID NO: 2, SEQ ID NO: 13, SEQ ID NO: 22, or SEQ ID NO: 24.

A preferred embodiment relates to the first and second aspects, wherein the one or more genomic chloramphenicol acetyl transferase gene(s) comprises a polynucleotide sequence which is at least 80% identical, 85% identical, 90% identical, 92% identical, 94% identical, 96% identical, 98% identical, or at least 99% identical to the sequence shown in SEQ ID NO: 1, SEQ ID NO: 12, SEQ ID NO: 21, or SEQ ID NO: 23.

In another preferred embodiment of the invention the selection marker of the DNA construct encodes a chloramphenicol acetyl transferase comprising an amino acid sequence at least 80% identical, 85% identical, 90% identical, 92% identical, 94% identical, 96% identical, 98% identical, or at least 99% identical to the sequence shown in SEQ ID NO: 2, SEQ ID NO: 13, SEQ ID NO: 22, or SEQ ID NO: 24.

Specific restriction enzymes or resolvases that excise portions of DNA, if it is flanked on both sides by certain recognition sequences known as resolvase sites or res-sites, are well known in the art, see e.g. WO 96/23073 (Novo Nordisk A/S) which is included herein by reference. It is preferred, that the selection marker of the DNA construct is flanked by resolvase-sites, preferably resolvase sites are res.

In a preferred embodiment of the first aspect, the selection marker of the DNA construct is flanked by nucleotide sequences that are recognized by a specific resolvase, preferably the nucleotide sequences are res; even more preferably the at least one marker gene is excised from the DNA construct by the action of a resolvase enzyme subsequent to selecting the host cell that grows under the selective conditions.

Preferably, the DNA construct of the invention further comprises a polynucleotide region that is sufficiently homologous with a genomic DNA region of the host cell to effect integration into the genome of the DNA construct by homologous recombination.

As exemplified below, it is also preferred that the inhibitory concentration of chloramphenicol in the growth-medium is at least 1 microgram/ml, preferably at least 2 microgram/ml, more preferably at least 3 microgram/ml, 6 microgram/ml, 9 microgram/ml, or at least 12 microgram/ml.

EXAMPLES

Example 1

Cat Deletion in Bacillus licheniformis PL1980

Construction of Deletion Plasmid

Primers were designed, based on the ATCC14580 genome sequence, to allow PCR amplification of a 0.5 kb segment 5' of the cat gene, and another 0.5 kb segment 3' of the cat gene. The DNA sequence of the cat-gene region of B. licheniformis ATCC14580 is shown in SEQ ID NO: 1, and the encoded protein is shown in SEQ ID NO: 2.

PCR amplifications were performed using DNA from *B. licheniformis* PL1980 as template, and READY-TO-GO™ PCR beads from Amersham Pharmacia Biotech, Inc., as described by the supplier, in the following program on a PTC-200 PCR machine from MJ Research:

| 1 cycle | 95° C. 2 minutes |
|---|---|
| 30 cycles | 94° C. 30 seconds |
| annealing | X° C. 1 minute (different temperatures were used in this step) |

72° C. 2 minutes, followed by 1 cycle of 72° C. for 5 minutes, whereafter reactions were cooled to 10° C.

The following primers were used:

```
SEQ ID NO: 3 (#449000):
5' cagtgaattcgtttaaccggcaattcttc

SEQ ID NO: 4 (#449001):
5' cagtgtcgacgtctcttaacatctctcac

SEQ ID NO: 5 (#448309):
5' cagtgtcgacctgcttcactgattccg

SEQ ID NO: 6 (#448315):
5' cagtaagcttaagattcctcgatgatttc
```

Initial PCR amplifications were not successful, no correctly sized fragments were obtained with either of the two primer combinations #449000+#449001 or #448309+#448315. Longer primers were designed:

```
SEQ ID NO: 7 (#450168):
5' cagtgaattcgtttaaccggcaattcttcaaacgtc

SEQ ID NO: 8 (#450169):
5' cagtgtcgacgtctcttaacatctctcactgctgtg

SEQ ID NO: 9 (#450170):
5' cagtgtcgaccgcttcactgattccggcaatattc

SEQ ID NO: 10 (#450171):
5' cagtaagcttaagattcctcgatgatttccaccacac

SEQ ID NO: 11 (#455882):
5' cagtgaattccgctttcgtttcaaatgacgg
```

These primers were used in a PCR reaction with an annealing temperature, which was ramped down from 62° C. to 53° C. in steps of 1° C., then kept at 57° C. for further 20 cycles.

The #450170+#450171 reaction gave a 0.5 kb fragment, which was digested with EcoRI+SalI, and ligated to EcoRI+SalI digested pUC19 (Yanisch-Perron et al., 1985, Gene 33(1): 103-119). The ligation mixture was transformed into *E. coli* SJ2 (Diderichsen et al., 1990, J. Bacteriol. 172(8): 4315-4321) by electroporation, and then selecting for ampicillin resistance. A clone was isolated having a sequence which was found to contain 23 differences as compared to the ATCC14580 sequence; this clone was kept and designated SJ7905 (SJ2/pSJ7905). The DNA sequence of the cat-gene region of *B. licheniformis* PL1980 is shown in SEQ ID NO: 12, and the encoded protein is shown in SEQ ID NO: 13.

The PCR with #450168+#450169 was not succesful. More PCR reactions across the entire cat gene region, with combinations of the above primers and a new primer, #455882, were then attempted, using the same annealing temperature regimen as in the above reactions. Primer combination #450171+#449000 gave an approximately 1.8 kb fragment; #450171+#450168 gave two fragments of approximately 1.7 kb and 1.1 kb, respectively; and #450171+#455882 gave a fragment of approximately 1.0 kb.

These four fragments were purified and each used as template in a reaction with primers #450170+#450171, using the annealing temperature regimen as above. All reactions gave a 0.5 kb fragment, as also found when this primer combination was used directly with chromosomal DNA as template, indicating that the four fragments were indeed fragments from the cat gene region.

The four long fragments were DNA sequenced. A schematic representation is given in FIG. 2. Based on the sequence, a new primer for the 3'-fragment was designed:

SEQ ID NO: 14 (#457708): 5' cagtgtcgacctgcttagcggtcttactg (corresponds to ATCC14580 cat 2 kb pos. 606-588, but with several mismatches).

The primer combination #457708+#450168 was used for amplification with the same annealing temperature regimen as above. The resulting 0.5 kb fragment was digested with SalI+EcoRI and cloned into SalI+EcoRI digested pUC19 vector which was transformed into *E. coli*. Two correct transformants of *E. coli* SJ2 were isolated and designated SJ8003 (SJ2/pSJ8003) and SJ8004 (SJ2/pSJ8004).

A pUC19 based plasmid, containing the assembled upstream and downstream fragments, was made by excision of the 0.5 kb SalI+HindIII fragment from pSJ7905, and insertion of this fragment into SalI+HindIII digested pSJ8003. Resulting transformants of *E. coli* SJ2 were isolated and designated SJ8011 (SJ2/pSJ8011) and SJ8012 (SJ2/pSJ8012).

The 5'cat-3'cat segment was then transferred onto a temperature sensitive, mobilizable integration vector by excision of the 0.9 kb EcoRI-HindIII fragment from pSJ8011, and ligation of this to the 4.3 kb EcoRI-HindIII fragment of pSJ2739 (U.S. Pat. No. 6,100,063) to provide the so-called deletion plasmid.

Correct transformants of *B. subtilis* DN1885 (Diderichsen et al., 1990, J. Bacteriol. 172(8), 4315-4321) comprising the deletion plasmid were isolated and designated SJ8017 (DN1885/pSJ8017) and SJ8018 (DN1885/pSJ8018).

Construction of a *B. licheniformis* PL1980-Derived Strain with a Deletion in the Cat Gene

*B. subtilis* conjugation donor strain PP289-5 (PP289-5 (U.S. Pat. No. 6,066,473) was transformed with the deletion plasmids, resulting in SJ8039 and SJ8040 (with pSJ8017), and in SJ8041 and SJ8042 (with pSJ8018).

*B. licheniformis* strain PP1897-3 is a derivative of *B. licheniformis* PL1980 which has an internal deletion in the alcalase gene, a deletion of most of the C-component protease coding region, and an artificially inserted promoter at the amyL, xylA and gntP loci. It was used as recipient in conjugations with the above two donor strains SJ8039 and SJ8040.

Conjugations were performed essentially as described in U.S. Pat. No. 6,066,473, selecting for erythromycin resistance. Tetracycline sensitive transconjugants were isolated, and chloramphenicol and erythromycin sensitive strains were isolated following integration and excision of the deletion plasmid.

Transconjugants were streaked onto LB PSG plates with erythromycin (5 mikrogram/ml) which were incubated at 50° C. overnight. The selection for erythromycin resistance at high temperature ensures that colonies formed have arisen by integration of the deletion plasmid into the *B. licheniformis* host strain chromosome by homologous recombination at either the 5' cat or the 3' cat sequence, because the plasmid is unable to replicate as a free plasmid at this temperature. Colonies were inoculated into TY liquid cultures and incubated at 30° C. overnight. This temperature allows the replication of the integrated plasmid, which facilitates its excision from the chromosome, and ultimately loss from the cell (indicated by erythromycin sensitivity).

The plasmid may excise via the same region of homology as was used for integration, in which case the resulting cell is identical to the host strain. Or the plasmid may alternatively excise via the other region of homology (e.g. integration via 5' cat, and excision via 3' cat, or vice versa) in which case the cat gene is deleted from the chromosome.

Aliquots of the overnight cultures were used to inoculate fresh TY cultures, and plated on LB PSG plates. Plates were incubated at 30° C. overnight, whereafter plates were replica plated to plates with and without erythromycin or chloramphenicol.

2 erythromycin sensitive and chloramphenicol sensitive strains were kept as SJ8071 (from donor SJ8039) and SJ8072 (from donor SJ8041). There was absolutely no growth of these deletion strains when reisolated onto LPBSG plates with 10 mikrogram/ml chloramphenicol, whereas there was some growth of a control strain reisolated onto the same plates.

Example 2

Cat Gene Deletion in the ATCC14580 Strain

A few attempts were made to introduce the cat-deletion into the ATCC14580 chromosome like it was done in the above, via integration and excision of a deletion plasmid introduced via conjugation from SJ8039-SJ8042. We obtained transconjugants and subsequently strains with integrated plasmids, but could not isolate the desired excision derivatives carrying the cat deletion. As this might be due to the sequence differences between the two different B. licheniformis strains in the cat gene region, a new deletion vector was constructed.

Construction of Deletion Plasmid

A boiled cell suspension of ATCC14580 was used as template in PCR reactions with primer combination #450168+#450169 (to give a fragment 3' of cat), and with primer combination #450170+#450171 (to give a fragment 5' of cat), using 57° C. as annealing temperature.

The 3' fragment was digested with EcoRI+SalI and ligated to EcoRI+SalI digested pUC19 vector, and the ligation mixture was transformed into E. coli SJ2 by electroporation. Transformants with the correct sequence of the cloned DNA were kept as SJ8151 (SJ2/pSJ8151) and SJ8152 (SJ2/pSJ8152).

The 5' fragment was digested with SalI+HindIII and ligated to SalI+HindIII digested pUC19 vector, and the ligation mixture transformed into E. coli SJ2 by electroporation. Transformants with the correct sequence of the cloned DNA were kept as SJ8153 (SJ2/pSJ8153) and SJ8154 (SJ2/pSJ8154).

The 5'cat-3'cat segment was assembled in a temperature sensitive, mobilizable integration vector by excision of the 0.5 kb EcoRI-SalI fragment from pSJ8151, and the 0.5 kb SalI-HindIII fragment from pSJ8153, and ligation of these two fragments to the 4.4 kb EcoRI-HindIII fragment of pSJ2739. Correct transformants of B. subtilis DN1885 were kept as SJ8209 (DN1885/pSJ8209) and SJ8210 (DN1885/pSJ8210).

Construction of B. licheniformis ATCC 14580 Strain with a Deletion in the Cat Gene B. subtilis conjugation donor strain PP289-5 was transformed with the integration vectors, resulting in SJ8221 and SJ8222 (with pSJ8209), and in SJ8223 and SJ8224 (with pSJ8210).

B. licheniformis strain ATCC14580 was used as recipient in conjugations with the above donor strains. Conjugations were performed as previously described, selecting erythromycin resistance.

Tetracycline sensitive transconjugants were isolated, and chloramphenicol and erythromycin sensitive strains isolated following integration and excision of the plasmid, as previously described. Two such strains were kept as SJ8343 (from donor SJ8222) and SJ8344 (from donor SJ8223).

Example 3

Test of Chloramphenicol Resistance

Strains PP1897-3, SJ8071 (=PP1897-3 delta cat), ATCC14580, and SJ8344 (=ATCC14580 delta cat) were propagated in 10 ml TY (WO 94/14968, p16) supplemented with 0.5% glucose at 30° C. overnight, with shaking. 50 microliter aliquots were used to inoculate further 10 ml TY+glucose cultures, supplemented with chloramphenicol (cam) to concentrations: 1 microgram/ml, 2 microgram/ml, 3 microgram/ml, 6 microgram/ml, 9 microgram/ml, or 12 microtram/ml, and incubation with shaking continued at 30° C. Growth was scored by visual inspection of turbidity after approximately 7 hours (table 1), and again after overnight incubation (table 2).

TABLE 1

| Strain | 1 µg/ml cam | 2 µg/ml cam | 3 µg/ml cam | 6 µg/ml cam | 9 µg/ml cam | 12 µg/ml cam |
|---|---|---|---|---|---|---|
| PP1897-3 | ++ | ++ | + | − | − | − |
| SJ8071 | + | − | − | − | − | − |
| ATCC14580 | ++ | + | + | − | − | − |
| SJ8344 | + | − | − | − | − | − |

After 7 hours incubation: ++) good growth, +) weak growth, −) no growth.

TABLE 2

| Strain | 1 µg/ml cam | 2 µg/ml cam | 3 µg/ml cam | 6 µg/ml cam | 9 µg/ml cam | 12 µg/ml cam |
|---|---|---|---|---|---|---|
| PP1897-3 | ++ | ++ | ++ | ++ | ++ | + |
| SJ8071 | ++ | ++ | ++ | + | + | + |
| ATCC14580 | ++ | ++ | ++ | ++ | ++ | + |
| SJ8344 | ++ | ++ | ++ | + | + | + |

After overnight incubation: ++) good growth, +) weak growth, −) no growth.

It is apparent that deletion of the putative chloramphenicol resistance gene, as done in strains SJ8071 and SJ8344, significantly decreases the chloramphenicol resistance of the strains.

Example 4

Use of Chloramphenicol Resistance for Transconjugant Selection

Construction of Test Plasmid with Chloramphenicol and Erythromycin Resistance Genes To investigate the potential use of chloramphenicol for tranconjugant selection, use was made of plasmid pSJ7976.

This plasmid is based on the mobilizable, temperature-sensitive vector backbone pSJ2739 mentioned previously, and contains the erythromycin resistance gene from pE194. It contains, in addition, the coding sequence of the pC194 cat gene inserted between segments, that flank the *B. licheniformis* C-component protease (U.S. Pat. No. 5,459,064, accession no. D10060, Kakudo et al., 1992, *J. Biol. Chem.* 267: 23782) gene 5' and 3'. It was constructed as follows:

A fragment 5' of the C-component protease gene was made by PCR amplification using chromosomal DNA from PL1980 as template, and an annealing temperature of 57° C. with the following primers:

```
SEQ ID NO: 15 (#448697):
5' gactaagcttagatcttcacttccttattttgttgtaagta

SEQ ID NO: 16 (#448698):
5' gactgaattcgtcgatcactttctgccactc
```

The PCR amplified fragment was digested with EcoRI+HindIII, ligated to EcoRI+HindIII digested pUC19, and the ligation mixture was transformed, by electroporation, into *E. coli* SJ2. Two correct transformants were kept as SJ7867 (SJ2/pSJ7867) and SJ7868 (SJ2/pSJ7868).

A fragment 3' of the C-component protease gene was made by PCR amplification using chromosomal DNA from PL1980 as template, and an annealing temperature of 57° C. with the following primers:

```
SEQ ID NO: 17 (#448699):
5' gactgaattcagatctgctagcacgcgtgcggccgcacgaagacagc
ccgcttc SEQ ID NO: 18 (#448700):
5' gactaagcttcataaattctcggatacaacac
```

The PCR amplified fragment was digested with EcoRI+HindIII, ligated to EcoRI+HindIII digested pUC19, and the ligation mixture transformed, by electroporation, into *E. coli* SJ2. Two correct transformants were kept as SJ7869 (SJ2/pSJ7869) and SJ7870 (SJ2/pSJ7870).

The C-component 5'- and 3'-flanking fragments were assembled in a temperature-sensitive, mobilizable integration vector by excision of the 0.5 kb EcoRI-BglII fragment from pSJ7867 and the 0.5 kb BglII-HindIII fragment from pSJ7869, and ligation of these fragments to the 4.4 kb EcoRI-HindIII fragment of pSJ2739. The ligation mixture was transformed into competent cells of *B. subtilis* DN1885, selecting erythromycin resistance (5 microgram/ml) at 30° C. Two correct transformants were kept as SJ7909 (DN1885/pSJ7909) and SJ7910 (DN 1885/pSJ7910).

The chloramphenicol resistance gene of pC194 was amplified by PCR from plasmid pDN1050 (Diderichsen et al., 1993, Plasmid 30, 312-315), using an annealing temperature of 57° C. with primers:

```
SEQ ID NO: 19 (#448716):
5' gactggatccatgaactttaataaaattgatttagac

SEQ ID NO: 20 (#448718):
5' gactgaattcgctagcacgcgttataaaagccagtcattaggcc
```

The PCR amplified fragment was digested with BamHI+EcoRI, ligated to BamHI+EcoRI digested pUC19, and the ligation mixture transformed, by electroporation, into *E. coli* SJ2. A correct transformant was kept as SJ7887 (SJ2/pSJ7887).

The pC194 cat gene was inserted between the 5' and 3' C-component flanking segments, by excision of the 0.7 kb BamHI-MluI fragment from pSJ7887 and ligation of this to the 5.4 kb BglII-MluI fragment of pSJ7909. The ligation mixture was transformed into competent *B. subtilis* DN1885 cells, selecting erythromycin (2 microgram/ml) and chloramphenicol (6 microgram/ml) resistance at 30° C. Two transformants were kept, SJ7975 (DN 1885/pSJ7975) and SJ7976 (DN 1885/pSJ7976).

Plasmid Introduction by Conjugation

The test plasmid, pSJ7976, which contains both chloramphenicol and erythromycin resistance genes, was transformed into the conjugative donor strain *B. subtilis* PP289-5, resulting in strain SJ8000.

*B. licheniformis* strains PP1897-3, the cat-deleted derivative SJ8071, strain ATCC14580, and the cat-deleted derivative SJ8344 were used as recipients in conjugations with donor strain SJ8000, essentially as described before.

For each donor/recipient combination, donor and recipient colonies were scraped off overnight plates and mixed in a small volume of liquid TY medium, and equal volumes from this mixture was plated on each of two LBPGS plates with D-alanine. Following 6 hours incubation at 30° C., one plate was replicaplated onto LBPGS with erythromycin (2 microgram/ml), and the other plate replica plated onto LPPGS with chloramphenicol (6 microgram/ml). These plates were incubated at 30° C. overnight, then left at room temperature (20-25° C.) for further 3 days.

After the overnight incubation, distinct colonies were observed on the plates with erythromycin for all donor/recipient combinations. There were approximately equal numbers on the plates with ATCC14580 and SJ8344, and there were about twice the number of colonies on the plates with PP1897-3 as compared to SJ8071.

The result using chloramphenicol selection was quite different. No distinct transconjugant colonies were observed with the two recipient strains containing intact, chromosomal chloramphenicol resistance genes, but the replica plates contained an even smear of cells.

Distinct transconjugant colonies were observed with the cat-deleted recipient strains. The number of transconjugants were the same when using chloramphenicol selection as when using erythromycin selection, for the SJ8071 recipient as well as for the SJ8344 recipient.

From each of the plates that contained distinct transconjugant colonies, whether by erythromycin or by chloramphenicol selection, 10 colonies were transferred to new plates with chloramphenicol or erythromycin, and all colonies were found to grow on both types of plates.

The use of cat-deleted recipient strains thus allows the succesful use of chloramphenicol resistance as selection for DNA introduction into *B. licheniformis*.

Example 5

DNA Sequence of the Cat-Gene of *B. licheniformis* 9945A

*Bacillus licheniformis* strain 9945A (Strain 5A2 from the *Bacillus* Genetic Stock Center; J. Bacteriology (1954) 68:307.) was obtained from Curtis B. Thorne and kept as JA102.

The chromosomal cat-gene region was PCR amplified using primers #450168+#450171, and the amplified fragment DNA was sequenced using the same primers. The resulting sequence is shown in SEQ ID NO: 21, and the encoded protein in SEQ ID NO: 22.

Example 6

DNA Sequence of the Cat-Gene DNA in Yet Another *B. licheniformis* Strain

International patent publication WO 03/083125 (Genencor Int. Inc) discloses the DNA and protein sequences of a chromosomal chloramphenicol resistance gene, on pages 21 and 22 of the text, with the DNA sequence given as SEQ ID NO: 58 and the protein sequence given as SEQ ID NO: 59 of that publication. The two sequences are also provided herein as SEQ ID NO: 23 and SEQ ID NO: 24, respectively.

Example 7

% Identity Alignments

The four different DNA sequences of the cat genes: cat ATCC14580, cat PL1980, cat 9945A, and cat WO 03/083125, were aligned in table 3. The matrix was calculated based on "all against all" alignments of the supplied sequences. The entry in row i and column j in the matrix is calculated as the number of exact matches in the alignment between sequence i and sequence j divided by the total length og the alignment minus the total length of the gaps in the alignment. Each alignment was done using the needle program from the EMBOSS package version 2.8.0. The program needle implements the global alignment algorithm described in the two references:

Needleman, S. B. and Wunsch, C. D. (1970) J. Mol. Biol. 48, 443-453.

Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley.

The alignments used the following parameters:

| | |
|---|---|
| Gap opening penalty: | 10.00 |
| Gap extension penalty: | 0.50 |
| Substitution matrix: | EBLOSUM62 |

TABLE 3

Alignment of the four *Bacillus licheniformis* cat-genes.

| %-Identity | ATCC14580 | PL1980 | 9945A | WO 03/083125 |
|---|---|---|---|---|
| ATCC14580 | 100.00 | 96.30 | 93.67 | 99.67 |
| PL1980 | | 100.00 | 92.59 | 96.33 |
| 9945A | | | 100.00 | 93.32 |
| WO 03/083125 | | | | 100.00 |

The four different protein sequences encoded by the above DNA sequences were also aligned as shown in table 4, using the same software and settings.

TABLE 4

Identity-alignment of the four proteins encoded by the DNA in table 3.

| %-Identity | ATCC14580 | PL1980 | 9945A | WO 03/083125 |
|---|---|---|---|---|
| ATCC14580 | 100.00 | 95.37 | 92.13 | 94.39 |
| PL1980 | | 100.00 | 90.28 | 90.82 |
| 9945A | | | 100.00 | 87.24 |
| WO 03/083125 | | | | 100.00 |

The invention claimed is:

1. A non-naturally occurring *Bacillus licheniformis* host cell comprising: a genome having one or more inactivated endogenous genomic chloramphenicol acetyl transferase gene(s); and a recombinant DNA construct comprising a selection marker encoding a chloramphenicol acetyl transferase.

2. The host cell of claim 1, wherein the recombinant DNA construct is plasmid, linearized plasmid, or linearized and concatamerized plasmid.

3. The host cell of claim 1, wherein the recombinant DNA construct further comprises a polynucleotide encoding a polypeptide of interest.

4. The host cell of claim 1, wherein the one or more genomic chloramphenicol acetyl transferase gene(s) encodes a chloramphenicol acetyl transferase with at least 90% sequence identity to SEQ ID NO: 2.

5. The host cell of claim 1, wherein the one or more genomic chloramphenicol acetyl transferase gene(s) comprises a polynucleotide sequence with at least 90% sequence identity to SEQ ID NO: 1.

6. The host cell of claim 1, wherein the selection marker of the DNA construct encodes a chloramphenicol acetyl transferase with at least 90% sequence identity to SEQ ID NO: 2.

7. The host cell of claim 1, wherein the selection marker of the DNA construct is flanked by resolvase sites.

8. The host cell of claim 1, wherein the DNA construct further comprises a polynucleotide region that is sufficiently homologous with a genomic DNA region of the host cell to effect integration into the genome of the DNA construct by homologous recombination.

9. The host cell of claim 1, wherein the DNA construct comprises a selection marker with at least 90% sequence identity to SEQ ID NO: 1.

10. The hot cell of claim 1, wherein the DNA construct comprises a selection marker with at least 94% sequence identity to SEQ ID NO: 1.

11. The host cell of claim 1, wherein the DNA construct comprises a selection marker with at least 96% sequence identity to SEQ ID NO: 1.

12. The host cell of claim 1, wherein the DNA construct comprises a selection marker with at least 98% sequence identity to SEQ ID NO: 1.

13. The host cell of claim 1, wherein the DNA construct comprises a selection marker with at least 99% sequence identity to SEQ ID NO: 1.

14. The host cell of claim 1, wherein the DNA construct comprises a selection marker consisting of SEQ ID NO: 1.

15. The host cell of claim 1, wherein the selection marker encodes a chloramphenicol acetyl transferase with at least 90% sequence identity to SEQ ID NO: 2.

16. The host cell of claim 1, herein the selection marker encodes a chloramphenicol acetyl transferase with at least 94% sequence identity to SEQ ID NO: 2.

17. The host cell of claim 1, wherein the selection marker encodes a chloramphenicol acetyl transferase with at least 96% sequence identity to SEQ ID NO: 2.

18. The host cell of claim 1, wherein the selection marker encodes a chloramphenicol acetyl transferase with at least 98% sequence identity to SEQ ID NO: 2.

19. The hot cell of claim 1, wherein the selection marker encodes a chloramphenicol acetyl transferase with at least 99% sequence identity to SEQ ID NO: 2.

20. The host cell of claim 1, wherein the selection marker encodes a chloramphenicol acetyl transferase consisting of SEQ ID NO: 2.

21. A non-naturally occurring *Bacillus licheniformis* host cell comprising a genome having one or more inactivated genomic chloramphenicol acetyl transferase gene(s); and a recombinant DNA construct comprising a selection marker encoding a chloramphenicol acetyl transferase with at least 96% sequence identity to SEQ ID NO: 2.

22. The host cell of claim 1, wherein the one or more genomic chloramphenicol acetyl transferase gene(s) comprises a polynucleotide sequence with at least 98% sequence identity to SEQ ID NO: 1, SEQ ID NO: 12, SEQ ID NO: 21, or SEQ ID NO: 23.

23. The hot cell of claim 1, wherein the one or more genomic chloramphenicol acetyl transferase gene(s) comprises a polynucleotide sequence with at least 99% sequence identity to SEQ ID NO: 1, SEQ ID NO: 12, SEQ ID NO: 21, or SEQ ID NO: 23.

24. The host cell of claim 1, wherein the one or more genomic chloramphenicol acetyl transferase gene(s) comprises a polynucleotide sequence consisting of SEQ ID NO: 1.

25. The host cell of claim 1, wherein the one or more genomic chloramphenicol acetyl transferase gene(s) comprises a polynucleotide sequence consisting of SEQ ID NO: 12.

26. The host cell of claim 1, wherein the one or more genomic chloramphenicol acetyl transferase gene(s) comprises a polynucleotide sequence consisting of SEQ ID NO: 21.

27. The host cell of claim 1, wherein the one or more genomic chloramphenicol acetyl transferase gene(s) comprises a polynucleotide sequence consisting of SEQ ID NO: 23.

28. The host cell of claim 21, wherein the one or more genomic chloramphenicol acetyl transferase gene(s) comprises a polynucleotide sequence with at least 99% sequence identity to SEQ ID NO: 1, SEQ ID NO: 12, SEQ ID NO: 21, or SEQ ID NO: 23.

29. A method for introducing a recombinant DNA construct into a modified *Bacillus licheniformis* host cell, the method comprising:
   a) providing a modified *Bacillus licheniformis* host cell, wherein one or more endogenous genomic chloramphenicol acetyl transferase encoding gene(s) has been inactivated;
   b) introducing a recombinant DNA construct comprising a selection marker encoding a chloramphenicol acetyl transferase into the modified host cell;
   c) cultivating the host cell of step (b) in a growth-medium comprising an inhibitory concentration of chloramphenicol; and
   d) selecting a host cell comprising the DNA construct that is capable of growing in the medium of step (c).

30. The method of claim 29, wherein the one or more genomic chloramphenicol acetyl transferase gene(s) encodes a chloramphenicol acetyl transferase with at least 90% sequence identity to SEQ ID NO: 2, SEQ ID NO: 13, SEQ ID NO: 22, or SEQ ID NO: 24.

31. The method of claim 29, wherein the one or more genomic chloramphenicol acetyl transferase gene(s) comprises a polynucleotide sequence with at least 90% sequence identity to SEQ ID NO: 1, SEQ ID NO: 12, SEQ ID NO: 21, or SEQ ID NO: 23.

32. The method of claim 29, wherein the selection marker of the DNA construct encodes a chloramphenicol acetyl transferase with at least 90% sequence identity to SEQ ID NO: 2, SEQ ID NO: 13, SEQ ID NO: 22, or SEQ ID NO: 24.

33. The method of claim 29, wherein the one or more genomic chloramphenicol acetyl transferase gene(s) encodes a chloramphenicol acetyl transferase with at least 99% sequence identity to SEQ ID NO: 2, SEQ ID NO: 13, SEQ ID NO: 22, or SEQ ID NO: 24.

34. The method of claim 29, wherein the one or more genomic chloramphenicol acetyl transferase gene(s) comprises a polynucleotide sequence with at least 99% sequence identity to SEQ ID NO: 1, SEQ ID NO: 12, SEQ ID NO: 21, or SEQ ID NO: 23.

35. The method of claim 29, wherein the selection marker of the DNA construct encodes a chloramphenicol acetyl transferase with at least 99% sequence identity to SEQ ID NO: 2, SEQ ID NO: 13, SEQ ID NO: 22, or SEQ ID NO: 24.

36. A process for producing an enzyme, comprising cultivating the *Bacillus licheniformis* host cell of claim 1, in a suitable medium to produce the enzyme.

* * * * *